United States Patent [19]

Starkweather

[11] 4,030,995

[45] June 21, 1977

[54] ALKALINE PHOSPHATASE ISOENZYME DETERMINATION

[75] Inventor: William H. Starkweather, Oakville, Mo.

[73] Assignee: Sigma Chemical Company, St. Louis, Mo.

[22] Filed: July 13, 1976

[21] Appl. No.: 704,831

[52] U.S. Cl. .................. 204/180 G; 204/180 S; 204/299 R; 23/230 B

[51] Int. Cl.² ........................................ G01N 27/26

[58] Field of Search ........... 204/180 G, 299, 180 S; 23/253 R, 230 B

[56] References Cited

UNITED STATES PATENTS

| | | | |
|---|---|---|---|
| 3,554,894 | 1/1971 | Zemel | 204/299 |
| 3,558,459 | 1/1971 | Granstrand et al. | 204/180 G |
| 3,607,695 | 9/1971 | Schneider | 204/180 S |
| 3,635,808 | 1/1972 | Elevitch | 204/180 G |
| 3,766,047 | 10/1973 | Elevitch | 204/299 |
| 3,808,118 | 4/1974 | Golias | 204/299 |
| 3,855,094 | 12/1974 | Teppo | 204/180 G |

*Primary Examiner*—Arthur C. Prescott
*Attorney, Agent, or Firm*—Polster and Polster

[57] ABSTRACT

Alkaline phosphatase isoenzymes are separated electrophoretically in agarose gels, or cellulose acetate membranes, equilibrated in a solution containing a low ionic strength buffer and a non-ionic detergent, such as Triton X-100. The electrophoretically separated isoenzymes are developed colorimetrically using 5-bromo-4-chloro-3-indolyl phosphate with a transphosphorylating buffer. Zones of enzyme activity appear as sharply-defined brilliant blue bands. The method is capable of resolving liver, bone, placental, intestinal and bile isoenzymes.

18 Claims, No Drawings

ALKALINE PHOSPHATASE ISOENZYME DETERMINATION

BACKGROUND OF THE INVENTION

This invention relates to an electrophoretic method of separating alkaline phosphatase isoenzymes.

The term "alkaline phosphatase" (abbreviated ALP), EC 3.1.3.1, is applied to a group of non-specific enzymes that hydrolyze monophosphoric esters of a variety of natural and synthetic compounds over a pH range of approximately 8.5 to 10.5. The different chemical species subsumed under the term alkaline phosphatase are referred to herein as isoenzymes of alkaline phosphatase. Alkaline phosphatase enzymes are found in many human tissues and in blood serum, and the isoenzyme composition of a given tissue is believed to be fixed genetically.

Determination of ALP has long been a routine clinical procedure as an aid in diagnosing various disease states. It was early recognized that identification of isoenzymes of ALP in serum can be a useful diagnostic tool for differentiating disease states characterized by increased serum ALP levels. Heat inactivation was first used to differentiate osteogenic (bone) ALP from the isoenzyme originating in hepatic (liver) tissue. In recent years, more delicate techniques for separating ALP isoenzymes have revealed several isoenzymes, some of which are present in elevated quantities in human sera even in non-pathologic conditions. For example, a "placental" ALP isoenzyme is elevated in serum during the last trimester of pregnancy; the same isoenzyme appears to be elevated in the serum of patients suffering from certain carcinomas. Likewise, the bone isoenzyme is elevated in growing children, as well as in patients suffering from certain bone diseases. Determination of ALP isoenzymes is now, therefore, important not only as a diagnostic tool, but also as a tool for basic biological and medical research.

In recent years, refinements in electrophoretic techniques have led to development of useful procedures for separating a number of ALP isoenzymes. In these procedures, a serum or tissue sample is applied to an appropriate support medium (such as agarose, polyacrylamide, cellulose acetate or starch gels) containing an appropriate electrolyte. When the gel is subjected to a differential electrical field, proteins within the sample acquire either a positive or negative charge and move toward the cathode or anode portion of the gel. Proteins in the sample are thus separated into more or less discrete fractions or bands. By the use of one or more reagents which react with the alkaline phosphatase bands to produce detectable products (such as colored products or products which have characteristic absorption bands in the ultraviolet spectrum), the bands of ALP isoenzymes are developed and identified.

Unfortunately, presently known electrophoresis techniques are generally not sensitive enough to separate and detect all of the ALP isoenzymes which may be present in a sample. The bands tend to be diffuse, lacking in intensity, and difficult to identify with particular isoenzymes. Furthermore, the procedures tend to be difficult and time-consuming to perform.

SUMMARY OF THE INVENTION

One of the objects of this invention is to provide an electrophoretic method of determining alkaline phosphatase isoenzymes which is capable of separating and developing at least the liver, bone, placental, intestinal and bile isoenzymes of ALP into well-defined bands.

Another object is to provide such a method which is simpler and faster than presently known methods.

Another object is to provide such a method which utilizes relatively stable reagents.

Another object is to provide such a method which produces permanent, intense, visible bands which may provide quantitative measures of ALP isoenzyme activity.

Other objects will become apparent in light of the following description.

In accordance with this invention, generally stated, an improved electrophoretic process for determining ALP isoenzymes is provided in which the electrophoretic support medium, preferably an agarose gel or cellulose acetate membrane, contains a buffer and a non-ionic detergent. In the preferred embodiments, the support medium is equilibrated in a solution containing the buffer and non-ionic detergent, the ALP-containing sample is applied to the support medium, a differential electric potential is imposed across the support medium to separate the ALP isoenzymes, and the separated isoenzymes are developed colorimetrically with a one-piece reagent that includes a phosphate ester of an indigo dye congener, a transphosphorylating buffer, and a soluble magnesium salt.

The process of the invention gives the desired clear separation of ALP isoenzyme bands, and the intensity of the bands, as measured by a densitometer, appears to give a quantitative measure of isoenzyme activity. The process also separates certain phenotypes (isoenzymes from a common tissue source), including some or all of the placental phenotypes.

The preferred support medium is an agarose gel. Agarose gels, at least those containing less than 3% agarose, have a pore size which is sufficiently large to avoid any sieving effect. They are easily prepared from non-toxic dry agarose, and are also available commercially as rehydratable agarose films and as hydrated films. In accordance with the present invention, a non-ionic detergent and a buffer are diffused through the gel. If the agarose gel is prepared from dry agarose, the dry agarose can be suspended in the buffer and heated to dissolve the agarose; the detergent can then be added while the agarose solution is cooling. Rehydratable agarose gels and pre-hydrated agarose gels are equilibrated with a solution containing the detergent and buffer.

Certain other support media are also usable in the process of the invention. For example, when some cellulose acetate membranes are equilibrated in a solution of non-ionic detergent and buffer, they produce the well-defined isoenzyme bands characteristic of the present invention, in the same order as on an agarose gel although not as widely separated. Among these cellulose acetate membranes are those sold by Millipore Corporation of Bedford, Massachusetts, and those sold by Beckman Instruments, Inc., of Fullerton, California. When certain other cellulose acetate membranes are equilibrated in a solution of non-ionic detergent and buffer, they do not produce the well-defined isoenzyme bands of the present invention. The differences between the cellulose acetate membranes which produce well-defined bands and those which do not is not at present understood. It has also been found that equilibrating a rehydratable polyacrylamide gel film in non-ionic detergent and buffer does not produce well-defined ALP isoenzyme bands.

A wide range of non-ionic detergents has been found to be usable. A molecular weight of about 600 to about 2,000 is preferred. For example, of the octylphenoxy polyoxyethanol detergents sold by Rohm & Haas under the trademark Triton, Triton X-100 (having approximately 10 ethyleneoxide residues) can be used at a concentration of about 2%, Triton X-165 (having about 16–17 residues) can be used at a concentration of about 1.3%, and Triton X-405 (having about 39–41 residues) can be used at a concentration of 0.7%. Polyoxyethylene ethers of fatty alcohols, sold by Atlas Chemical Industries under the trademark Brij, are also usable. For example, Brij 96 (containing oleyl alcohol and about 10 ethylene oxide residues) can be used at a concentration of about 2%. The polyoxyethylene sorbitan monolaurate (having about 20 ethylene oxide residues) sold by Atlas Chemical Industries as Tween 20 can also be used at a concentration of 2%.

The buffer is preferably a low ionic strength buffer, having an ionic strength of less than 0.05, and most preferably one having an ionic strength in the range of 0.020 to 0.025. An example of such a buffer is a tris(-hydroxymethyl)aminoethane/barbital buffer, pH 8.8. Higher ionic strength buffers provide more sharply defined isoenzyme bands, but generate more heat during electrophoresis and thus require active cooling of the electrophoresis cell. Active cooling requires a considerably more complex instrument than is available in most laboratories.

Application of samples to the support medium may be by such standard methods as cutting a slot in the gel to apply the untreated sample, inserting the untreated sample in pre-formed wells in the support medium, applying a mixture of gel and sample to a slot or well in the support medium, or applying the sample to the surface of the support medium, as with an overlay template. Addition of detergent to the sample is not necessary for the success of the process of the present invention, and in fact has no detectable effect in the preferred embodiments. The sample is preferably human serum or heparinized plasma. Plasma should be centrifuged to remove platelets. Alkaline phosphatase activity of samples stored frozen for extended periods can be restored by incubation for six hours at 37° C.

A marker solution, containing known amounts of the isoenzymes expected to be found in the sample under test, is conveniently applied to the support medium at the same time as the test sample. The marker solution may be a previously assayed human serum sample, for example. For identifying placental ALP phenotypes, separate markers representing each phenotype are used.

After the sample is applied to the support medium, electrophoresis is carried out in an electrophoresis cell filled with the appropriate volume of cold buffer solution. A differential electric potential, on the order of 9 to 15 volts per centimeter for agarose gels and somewhat higher for cellulose acetate membranes, is applied across the support medium for about 30 to 60 minutes. The voltage applied and the duration of its application depend to some extent on the electrophoresis cell and the support medium utilized, and are chosen in accordance with standard electrophoresis practice.

When electrophoresis is completed, the ALP isoenzyme bands are developed so that they can be detected either visually or by a suitable instrument. The colorimetric procedure of the preferred embodiment of the invention involves addition of a one-piece reagent system to produce intense colored bands. The reactivity of the colorimetric reagent system closely parallels that of p-nitrophenyl phosphate, which is commonly employed as a substrate for colorimetric total alkaline phosphatase procedures. The one-piece reagent system includes a phosphate ester of an indigo congener, preferably a 3-indolyl phosphate salt, and most preferably a halogenated derivative of 3-indolyl phosphate such as 5-bromo-4-chloro-3-indolyl phosphate. It also includes a soluble magnesium salt, because magnesium ions are known to be required for phosphatase activity, and a transphosphorylating buffer. The transphosphorylating buffer is preferably an amino alcohol. The presently preferred transphosphorylating buffer is 2-amino-2-methyl-1-propanol (AMP), but other amino alcohols such as diethanol amine (DEA), ethane amino ethanol (EAE) and 2-amino-2-methyl-1,3-propandiol (AMPD) are also usable. Alkaline phosphatase dephosphorylates the indolyl phosphate dye, and it dimerizes to form a highly colored product. The phosphorylation of the indolyl is believed to be accompanied by phosphorylation of a serine residue of the enzyme near the active site of the enzyme. The inorganic phosphate is then transferred by transphosphorylation from the enzyme to the amino alcohol buffer. By this mechanism, accumulation of phosphate by the enzyme and consequent inhibition of the enzyme are avoided.

DESCRIPTION OF THE PREFERRED EMBODIMENT

The following Examples are illustrative of the presently preferred process of this invention.

EXAMPLE 1

The following reagents are made up:

A. Surfactant Solution
   Triton X-100 (octylphenoxy polyoxyethanol having approximately 10 polyoxyethanol residues) 10% v/v in distilled water.
   (Stored at room temperature.)

B. Tris-Barbital Buffer (pH 8.8)
   Tris(hydroxymethyl)aminomethane; 0.15 mole
   Sodium diethylbarbiturate; 0.15 mole
   Diethylbarbituric acid; 0.042 mole
   Deionized water; 1,500 ml.
   (Stored in refrigerator at 0°–5° C.)

C. Equilibration Buffer Solution
   Surfactant solution (Reagent A); 2 parts
   Tris barbital buffer (Reagent B); 2 parts
   Deionized water; 6 parts
   (Stored in refrigerator at 0°–5° C.)

D. BCIP Phosphatase Substrate Solution
   5-bromo-4-chloro-3-indolyl phosphate, p-toluidine salt; 2.3 mmol/liter
   Magnesium asparatate; 0.1 mmol/liter
   2-amino-2-methyl-1-propanol; 150 mmol/liter
   (Stored in refrigerator at 0°–5° C.)

E. Methanol/Acetic Acid Solution
   Methanol; 75 ml.
   Glacial acetic acid; 5 ml.
   Water; 20 ml.

A rehydratable agarose film, as supplied by Beckman Instruments, Inc., is rehydrated in a beaker containing 480 ml. deionized water and 120 ml. surfactant solution (Reagent A). After rehydration, the gel is removed from solution and blotted gently. The gel is then immersed in Equilibration Buffer Solution (Reagent C) for thirty minutes. The gel is then blotted gently to eliminate excess moisture. Five microliters of serum to be tested and five microliters of marker solution (containing known quantities of ALP isoenzymes) are applied to the gel at aligned "start" positions, using the Beckman Instrument "Multiple Sample Applicator System" at "—0—" setting. After the samples have diffused into the gel, the samples are applied a second time. The gel is placed in a Bioware "Cool Pak" electrophoresis cell (Bioware, Inc., Wichita, Kansas) filled with the appropriate volume of cold Electrophoresis Buffer Solution (Reagent B). Care is taken to make appropriate contact with the buffer solution. A potential of one hundred fifty volts (DC) (15 volts per centimeter) is applied across the cell for 45 minutes.

On completion of electrophoresis, the agarose gel is removed from the cell and placed in a suitable container, such as a small covered tray. To the container is added 30 ml. of BCIP Phosphatase Substrate Solution (Reagent D), to cover the gel. The gel is incubated at 37° C. for forty-five minutes, to develop colored bands at the positions of ALP activity. The gel is then removed from the substrate solution and placed in a container holding 200 ml. of Methanol Acetic Acid Solution (Reagent E) for thirty minutes at room temperature, to stop the color development reaction. The gel is then washed in 200 ml. of distilled water for thirty minutes at room temperature. The gel is then dried in a forced air incubator at 60°–70° C. for fifteen to thirty minutes. The gel is then observed as a transparent film carrying bright blue bands representative of ALP isoenzymes. The bands representing the liver, bone, placental, intestinal and bile ALP isoenzymes, if all of the isoenzymes are present in the test sample, appear as separate and well-defined bands. Likewise, although placental ALP phenotypes migrate nearly the same distance, only one phenotype is present in any sample, and its band is sharp enough to be identified with (or distinguished from) the phenotype band of the marker solution. The identity of the bands is easily determined by comparison with the marker. Densitometer readings for the colored bands give a quantitative measure of the relative amounts of the isoenzymes.

EXAMPLE 2

A cellulose acetate membrane, supplied by Beckman Instruments, Inc., as Product No. 324330, is equilibrated in 50 ml. of Equilibration Buffer Solution (Reagent C) for five minutes. The marker solution and test sample of Example 1 are applied to the surface of the membrane with a commercially available sample applicator. The membrane is then placed in a Bioware "Cool Pak" electrophoresis cell filled with Electrophoresis Buffer Solution (Reagent B), and an electrical potential of 250 volts (25 volts per centimeter) is imposed across the membrane for thirty minutes. Upon completion of electrophoresis, the membrane is removed from the electrophoresis cell and color is developed by an agar overlay technique. A 2% agar gel is prepared by heating the agar in AMP buffer (300 mmol/liter) containing magnesium aspartate (0.2 mmol/liter). The agar solution is allowed to cool to 45° C. and an equal volume of BCIP solution (4.6 mmol/liter) is added. The solution is immediately poured into a tray and allowed to gel. The cellulose acetate membrane containing the separated isoenzyme fractions is carefully overlayed on the surface of the agar gel and permitted to stand for thirty minutes at 37° C.

The colored bands produced on the cellulose acetate membrane are in the same relative positions as the bands produced on the agarose gel support medium of Example 1. However, the bands are somewhat less defined and are not separated by as great a distance as in Example 1. The membrane is also opaque. Quantification of the isoenzymes is therefore more difficult. However, the bands are substantially better defined than are those obtained using previously known procedures.

Although the foregoing Examples represent the best means presently known for carrying out the process of the invention, numerous variations in the process of this invention, within the scope of the appended claims, will occur to those skilled in the art in light of the foregoing disclosure.

I claim:

1. In an electrophoretic process of determining alkaline phosphatase isoenzymes in a sample comprising a step of applying said sample to a support medium, a step of subjecting the support medium to a differential electric potential to separate said isoenzymes, and a step of rendering said isoenzymes detectable, the improvement wherein said support medium is chosen from the group consisting of agarose gels and cellulose acetate membranes, said support medium containing a buffer and a non-ionic detergent diffused through it.

2. The process of claim 1 wherein said non-ionic detergent has a molecular weight of from about 600 to about 2000.

3. The process of claim 1 wherein said buffer is a low ionic strength buffer, having an ionic strength of less than 0.05, and buffering said support medium to a pH of from 8 to 9.

4. The process of claim 1 wherein said buffer has an ionic strength from about 0.020 to about 0.025.

5. The process of claim 1 wherein said support medium is an agarose gel containing less than 3% agarose by weight.

6. The process of claim 5 wherein said agarose gel is equilibrated in a solution of said buffer and said non-ionic detergent.

7. The process of claim 1 wherein said support medium is a cellulose acetate gel equilibrated in a solution of said buffer and said non-ionic detergent.

8. An electrophoretic method capable of separating into well-defined, easily observed, discrete fractions at least the liver, bone, placental, intestinal and bile alkaline phosphatase isoenzymes in a biological fluid, said method comprising a step of applying a sample of said fluid to a support medium containing a buffer and a non-ionic detergent; imposing a differential electric potential across the support medium; and a subsequent dyeing step, said dyeing step comprising the addition of a phosphate ester of an indigo congener stain, an activating amount of a soluble magnesium salt and a transphosphorylating buffer.

9. The method of claim 8 wherein said support medium is chosen from the group consisting of agarose gels and cellulose acetate membranes.

10. The method of claim 9 wherein said medium is prepared by equilibration in a solution containing said buffer and said detergent.

11. The method of claim 9 wherein said non-ionic detergent has a molecular weight of from about 600 to about 2,000.

12. The method of claim 11 wherein said buffer has an ionic strength from about 0.020 to about 0.025.

13. The method of claim 9 wherein said method is also capable of separating placental alkaline phosphatase phenotypes.

14. The method of claim 9 wherein said transphosphorylating buffer is an amino alcohol.

15. The method of claim 14 wherein said transphosphorylating buffer is chosen from the group consisting of AMP, DEA, EAE and AMPD.

16. The method of claim 9 wherein said stain is chosen from the group consisting of soluble salts of 3-indolylphosphate and derivatives thereof.

17. The method of claim 16 wherein said stain is a soluble salt of a halogenated 3-indolyl phosphate.

18. The method of claim 9 wherein said medium is an agarose gel equilibrated in a solution containing a low ionic strength buffer and a non-ionic detergent.

* * * * *